United States Patent [19]

Dobson

[11] Patent Number: 4,937,384

[45] Date of Patent: Jun. 26, 1990

[54] PROCESS FOR THE PRODUCTION OF AMINES

[75] Inventor: Ian D. Dobson, North Humberside, United Kingdom

[73] Assignee: BP Chemicals Limited, London, England

[21] Appl. No.: 168,852

[22] Filed: Mar. 16, 1988

[30] Foreign Application Priority Data

Mar. 26, 1987 [GB] United Kingdom ................. 8707305

[51] Int. Cl.$^5$ ............................................ C07C 209/50
[52] U.S. Cl. ...................... 564/488; 564/375; 564/448
[58] Field of Search .................. 564/375, 448, 488

[56] References Cited

U.S. PATENT DOCUMENTS

| | | | |
|---|---|---|---|
| 2,867,628 | 1/1959 | Cass | 260/346.8 |
| 3,845,130 | 10/1974 | Suggitt | 260/583 |
| 4,307,248 | 12/1981 | Barnett et al. | 564/358 |
| 4,429,157 | 1/1984 | Disteldorf et al. | 564/446 |
| 4,448,998 | 5/1984 | King | 564/488 |

OTHER PUBLICATIONS

Wojcik et al *J. Amer. Chem Soc.* voll LVI, (1934) pp. 2419–2424 "Catalytic Hydrogenation of Amides to Amines".

Engels et al. *Chem Abst.* vol. 88, (1978) abstract #88:12468p "Dispersity and activity of Pa/Re/Alumina catalysts".

*Primary Examiner*—Richard L. Raymond
*Assistant Examiner*—P. O'Sullivan
*Attorney, Agent, or Firm*—Brooks Haidt Haffner & Delahunty

[57] ABSTRACT

An amine is produced by reacting an amide with hydrogen at elevated temperature in the presence as catalyst of a composition comprising as a first component (i) a noble metal of Group VIII of the Periodic Table of the Elements, particularly palladium or ruthenium, and (ii) rhenium, which component may be supported, and as a second component either an alumina or a zeolite, preferably a low silica aluminosilicate zeolite, for example type A or type Y zeolite.

15 Claims, No Drawings

PROCESS FOR THE PRODUCTION OF AMINES

The present invention relates generally to the production of amines by the hydrogenation of amides and in particular to the use an improved catalyst composition in amines production.

The production of amines by the hydrogenation of amides, which may be represented by the following overall reaction:

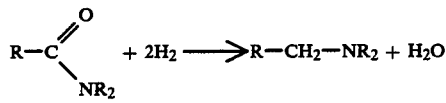

R being independently either hydrogen or alkyl, is a known reaction, though it has not been extensively studied. The use of copper chromite as catalyst has been reported, see for example U.S. Pat. Nos. 3,190,929 and 3,444,204 and Wojcik et al, J.A.C.S. 56; 2419, (1934). The processes described therein are characterised by low activity even at 260° C. and 2100 psig hydrogen pressure. In U.S. Pat. No. 4,448,998 the use of a zeolite (4A) as co-catalyst together with copper chromite is described. In French Patent No. 1,532,063 there is described the use of ruthenium/alumina as a catalyst and dioxane as an inert solvent for the amide. The selectivity to amines using the process of the French patent appears to be inferior to that obtained in U.S. Pat. No. 4,448,998. The use of rhenium metal (reduced rhenium (VI) oxide) as a catalyst is described in J. Org. Chem. 2345, (1963) by H. S. Broadbent et al.

We have now surprisingly found an improved catalyst for the hydrogenation of amides which can substantially overcome the low activity and selectivity to the desired amine products generally associated with prior art catalysts.

Accordingly, the present invention provides a process for the production of an amine which process comprises reacting an amide with hydrogen at elevated temperature in the presence as catalyst of a composition comprising as a first component (i) a noble metal of Group VIII of the Periodic Table of the Elements, and (ii) rhenium, and as a second component either an alumina or a zeolite.

The amide reactant may be an amide of the formula:

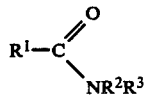

(I)

wherein $R^1$ is either hydrogen or a benzyl, aryl, aliphatic or cycloaliphatic group which may be substituted or unsubstituted, and $R^2$ and $R^3$ are independently either hydrogen or aliphatic groups which may be substituted or unsubstituted. Preferably $R^1$ is either hydrogen or an alkyl group. $R^2$ and $R^3$ are preferably either hydrogen or alkyl groups. Examples of amides suitable for use in the process of the invention include acetamide, propionamide and also those amides generally referred to as fatty amides, typically higher than $C_7$. It will be appreciated that in theory when $R^2=R^3=H$, the product comprises a primary amine, when either of $R^2$ and $R^3=H$ and the remaining one of $R^2$ and $R^3$ is alkyl, for example, the product comprises a secondary amine and when $R^2=R^3=$alkyl, for example, the product comprises a tertiary amine, though in practice a mixture of amines may be formed. Because of their relative commercial usage, it is often desirable to produce primary amines.

Commercially available hydrogen may be used with or without further purification.

The process is preferably operated in the liquid phase, if desired using an inert solvent. Suitable inert solvents include oxygenated solvents, such as for example dioxane and tetrahydrofuran.

The catalyst comprises a first component which is (i) a noble metal of Group VIII of the Periodic Table of the Elements and (ii) rhenium and a second component which is a zeolite. As regards the first component, for the avoidance of doubt the noble metals of Group VIII for the purpose of the present invention are considered to be palladium, platinum, rhodium, ruthenium, iridium and osmium. Of the aforesaid metals of Group VIII, palladium and ruthenium are preferred.

Preferably the first component further includes a support. Suitable supports include high surface area graphitised carbons, graphites, activated carbons, silicas, aluminas and silica/aluminas, of which high surface area graphitised carbons and silicas are preferred. Preferred silica supports are those having a high surface area, typically greater than 50 m²/g. However, low surface area supports may also be used.

Typical of the high surface area graphitised (HSAG) carbons are those described in GB-A-2136704 (BP Case No. 5536). The carbon is preferably in powdered or particulate form. The size of the carbon particles will depend on the reactor type used.

The HSAG carbons are porous carbons. They may be characterised by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473–498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred HSAG carbons have a BET surface area of at least 100 m²/g, more preferably at least 200 m²/g, most preferable at least 300 m²/g. The BET surface area is preferably not greater than 1000 m²/g, more preferably not greater than 750 m²/g.

The ratio of BET to basal plane surface area is preferably not greater than 4:1, more preferably not greater than 2.5:1. It is particularly preferred to use carbons with ratios of BET to basal plane surface area of not greater than 1.5:1.

It is preferred to use carbons with ratios of basal plane surface area to edge surface area of at least 10:1, preferably at least 100:1. It is not believed that there is an upper limit on the ratio, although in practice it will not usually exceed 200:1.

The preferred HSAG carbon support may be prepared by heat treating a carbon-containing starting material. The starting material may be an oleophillic graphite e.g. prepared as disclosed in GB 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than those indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidising agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidising agents are steam, carbon dioxide, and gases containing molecular oxygen e.g. air. The oxidation is preferably carried out to give a carbon weight loss of at least 10% wt based on weight of carbon subjected to the oxidation step, more preferably at least 15% wt.

The weight loss is preferably not greater than 40% wt of the carbon subjected to the oxidation step, more preferably not greater than 25% wt of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

Suitably the first component comprises from 0.1 to 10% by weight Group VIII noble metal, preferably from 0.5 to 5% by weight Group VIII noble metal, and from 0.1 to 20% by weight rhenium, preferably from 1 to 10% by weight rhenium, the remainder of the first component comprising the support.

The first component may be further modified by the incorporation of a metal or metals of Group IA, Group IIA or Group IVA, preferably by a metal of Group IA of the Periodic Table of the Elements. A suitable metal is potassium. The amount of the modifying metal(s) may suitably be in the range from 0.1 to 20% by weight based on the total weight of the first component. The addition of a modifying metal can have the advantageous effect that carbon-carbon bond hydrogenolysis can be supressed to a greater or lesser extent during the hydrogenation, thereby improving the selectivity of the process to desired products.

The first component may be prepared by a variety of methods. One method of preparation comprises impregnating the support with an aqueous solution of soluble compounds of rhenium and the Group VIII noble metal which compounds are thermally decomposable/reducible to the metal and/or metal oxide.

Impregnation may be by way of co-impregnation or sequential impregnation, preferably by sequential impregnation. Sequential impregnation is preferably effected in the order Group VIII noble metal followed by rhenium.

A preferred method of producing the first component comprises the steps of:

(A) impregnating a support with a solution of a soluble Group VIII noble metal compound thermally decomposable/reducible to Group VIII noble metal and subsequently removing the solvent therefrom, and (B) impregnating the Group VIII metal impregnated support with a solution in a solvent in which the Group VIII metal is substantially insoluble of a soluble rhenium compound thermally decomposable/reducible to rhenium metal and/or an oxide and thereafter removing the solvent therefrom.

Water may suitably be employed as the solvent in step (A) and a lower alkanol, for example ethanol, may be used as the solvent in step (B). The production of a catalyst in the aforesaid manner can avoid the palladium impregnated on the support in step (A) being leached to any appreciable extent in step (B) of the process.

Another preferred method of producing the first component comprises the steps of:

(A') impregnating a support with a solution of a soluble Group VIII noble metal compound thermally decomposable/reducible to the Group VIII noble metal and subsequently removing the solvent therefrom, (B') heating the Group VIII noble metal on the support, and (C') impregnating the Group VIII noble metal impregnated support with a solution of a soluble rhenium compound thermally decomposable/reducible to rhenium metal and/or oxide and thereafter removing the solvent therefrom.

The Group VIII noble metal on the support may suitably be heated in the presence of either an inert gas, for example nitrogen, a reducing gas, for example hydrogen, or an oxygen-containing gas, for example air. Heating in the presence of an inert gas may suitably be accomplished at an elevated temperature in the range from 150° to 350° C. Heating in the presence of a reducing gas may suitably be accomplished at an elevated temperature in the range from 100° to 350° C. Heating in the presence of an oxygen-containing gas may suitably be accomplished at an elevated temperature in the range from 100° to 300° C., provided that when a high surface area graphitised carbon is used as support the upper temperature limit is 200° C.

In this embodiment of the invention it is not necessary that a solvent in which the Group VIII metal is substantially insoluble be used in step (C') of the process. Thus any suitable solvent may be used in steps (A') and (C') of the process. Suitable solvents include independently water and alkanols.

An advantage of the heating step (step (B')) is that the noble metal of Group VIII is rendered less prone to leaching in step (C') of the process.

Preferably, a further step is interposed either between step (A) and step (B) or between step (A') and step (B') wherein the Group VIII noble metal impregnated support is dried, suitably by heating at a temperature in the range from 50° to 150° C. It will be appreciated by those skilled in the art that this step may be incorporated into step (B'), if desired.

Suitable Group VIII noble metal compounds which are decomposable/reducible to the metal include salts of the metals, for example carboxylates, nitrates and compounds in which the Group VIII noble metal is present in the anion moiety, for example ammonium tetrachloropalladate and ammonium tetranitropalladate. Suitable rhenium compounds which are decomposable/reducible to rhenium metal and/or oxide include dirhenium decacarbonyl, ammonium perrhenate and rhenium heptoxide.

The metal of Group IA, Group IIA or Group IVA of the Periodic Table of the elements may be added to the first component at any point during its preparation. Thus, the supported palladium/rhenium catalyst may be impregnated with a solution of a soluble compound of the metal. Alternatively, a soluble compound of the metal may be added to the co-impregnation solution or either of the sequential impregnation solutions.

A preferred first component comprises palladium and rhenium supported on a high surface area graphitised carbon of the type described in the aforesaid GB-A-2136704.

Before use in the process of the invention the first component is preferably activated by contact at elevated temperature with either hydrogen or a hydrogen-/inert gas, for example nitrogen, mixture for a period of from 1 to 20 hours. The elevated temperature may suitably be in the range from 200° to 350° C.

Whilst the precise nature of the first component on the support can not be determined with any degree of confidence, it is believed that the Group VIII noble metal component is in the form of the elemental metal and the rhenium component is in the form of the elemental metal and/or an oxide thereof.

The second component of the catalyst composition is either an alumina or a zeolite, preferably a zeolite. The zeolite may suitably be any metallotectosilicate zeolite, for example an aluminosilicate zeolite or a gallosilicate zeolite. A preferred zeolite is an aluminosilicate zeolite which may be of the low silica type, i.e. one having a silica to alumina molar ratio of less than 10:1, or of the high silica type, i.e. one having a silica to alumina molar ratio of greater than 10:1. Preferably the zeolite is a low silica aluminosilicate zeolite, for example zeolite type A or zeolite type Y. A preferred zeolite is a zeolite type A, of which zeolite type 4A is particularly useful. Type A zeolites are readily available on a commercial scale. A suitable alumina is gamma-alumina.

The catalyst composition useful in the performance of the invention may suitably be produced by mixing, preferably intimately, the first component with the second component.

The ratio of the second component of the catalyst composition to the first component may be varied over a wide range. A typical ratio is about 4:1.

The process is operated at an elevated temperature, which may suitably be in the range from 150° to 300° C., preferably from 175° to 225° C.

The hydrogen pressure may suitably be in the range from about 200 to 3000 psig, preferably from 400 to 2000 psig, though higher and lower pressures may be employed.

The process may be operated batchwise or continuously, the preference for which will depend on the nature of the amide to be hydrogenated.

The process of the present invention will now be further illustrated by reference to the following Examples and Comparison Tests.

CATALYST PREPARATION

A catalyst composition according to the invention was prepared according to the procedure outlined below. In the procedure, HSAG carbon denotes high surface area graphitised carbon, prepared and characterised as follows:

The carbon used as support was prepared from a commercially available activated carbon sold by Degussa under the designation BK IV. The activated carbon was heat treated as follows. The carbon was heated from room temperature in a stream of argon to 1700° C. over a period of about one hour. When the temperature reached 1700° C. the carbon was allowed to cool in the stream of argon to 25° C. The carbon was then heated in air in a muffle furnace at approximately 520° C. for a time known from experience to give a weight loss of 20% wt. The carbon was then heated in argon to between 1800° C. and 1850° C. The carbon was allowed to cool to room temperature in an argon atmosphere. The resulting graphite-containing carbon was then ground to 16–30 mesh BSS.

The resulting carbon had the following properties:
BET surface area: 710 m$^2$/g
basal plane surface area: 389 m$^2$/g
edge surface area: 2.3 m$^2$/g
BET/basal surface area ratio: 1.83
basal plane/edge surface area ratio: 169

The carbon was pre-treated as follows: to the carbon was added HCl (10% by volume and the mixture refluxed for 5 hours, following which it was washed with water. This was then repeated. It was then refluxed with water for 5 hours, washed with water and finally dried.

Pd/Re/HSAG

In the following procedure nominal loading is defined as weight of metal (not salt) added to the support expressed as a percentage of the weight of support.

An aqueous solution of palladium nitrate was added to HSAG carbon, the solvent was removed on a rotary evaporator, and the resulting impregnated carbon catalyst dried overnight at 100° C. in a vacuum oven. The catalyst was then cooled and transferred to a quartz tube, and was then heated in a stream of hydrogen from ca 30° to 280° C. over a period of six hours. After ten hours at 280° C., the catalyst was cooled under hydrogen, and then purged for several hours with nitrogen.

The palladium on carbon was then mixed with an aqueous solution of $Re_2O_7$, the solvent again removed on a rotary evaporator, and the catalyst dried overnight at 100° C. in a vacuum oven. The amounts of palladium nitrate and rhenium heptoxide were chosen to give nominal loadings of 2.5% Pd and 5% Re in the first component of the catalyst.

The first component of the catalyst was then activated by heating at atmospheric pressure in a stream of hydrogen to either 280° or 300° C. over a two hour period, and then holding at the final temperature for one hour. After activation, the catalyst was cooled in hydrogen.

The activated first component (0.5 g) was then mixed with type 4A zeolite (ex BDH) (2.0 g) to form the final catalyst composition.

EXAMPLE 1 AND COMPARISON TESTS A AND B

This Example demonstrates that both the palladium/rhenium on carbon and the zeolite are necessary for a satisfactory catalyst system.

A 70 ml magnetically stirred autoclave was charged with 2 g of propionamide and 5 g of 1,4-dioxane (an inert solvent for the amide). Catalyst was added as indicated in Table 1. The autoclave was connected to a gas manifold and was pressurised with hydrogen. The heating period and reaction temperature are listed in Table 1. After cooling the product mixture was analysed by gas liquid chromatography. Conversion is defined as the percentage of amide which is converted to products.

TABLE 1

| Example | Catalyst | H$_2$ Pressure (psig) | Temp (°C.) | Time (h) | Conv. (%) | Selectivity to amines (%) |
|---|---|---|---|---|---|---|
| Comp Test A | 2.0 g 4A zeolite | 3000 | 200 | 6 | 0 | — |
| Comp Test B | 0.5 g Pd/Re/HSAG | 4000 | 200 | 8 | 9 | 100 |
| 1 | 0.5 g Pd/Re/HSAG plus 2.0 g 4A zeolite | 4000 | 200 | 6 | 96 | 74.4 |

EXAMPLE 2 AND COMPARISON TEST C

This Example demonstrates the improved activity and selectivity of the catalyst system of the invention compared to the system of U.S. Pat. No. 4,448,998.

The reaction was performed as described in Example 1. In each case 2 g of zeolite 4A and 0.5 g of metal catalyst was used. Reaction was for 6 hours at 250° C. under a hydrogen pressure of 4000 psig.

Results are given in Table 2.

EXAMPLES 3 AND 4

These Examples demonstrate that the reaction can be satisfactorily performed at 200° C. This is substantially lower than the preferred range in U.S. Pat. No. 4,448,998 i.e. 260° to 310° C.

The reaction was performed as described in Example 1.

In each case, 2 g of zeolite 4A and 0.5 g of 2.5% Pd/5% Re on high surface area graphite support was used as the catalyst system. Reaction was for 6 hours. Temperature and pressure were as indicated in Table 3. Results for the Example are given in Table 3.

EXAMPLE 5

The procedure of Example 1 was repeated using 0.5 g of a 2% Pd/10% Re on activated carbon (ex Engelhard) catalyst instead of the Pd/Re/HSAG catalyst. The results, together with the appropriate result from Example 1 are given in Table 4.

With reference to Table 4, the conversion using an activated carbon support is very much lower than that achieved using an HSAG support.

TABLE 2

| Example | Catalyst | Conversion (%) | Selectivity (%) monopropylamine | dipropylamine | tripropylamine | Amines Productivity kg/kg catalyst/h |
|---|---|---|---|---|---|---|
| 2 | 2.5% Pd/5% Re/HSAG | 99 | 2.7 | 44.4 | 17.9 | 0.429 |
| Comp Test C | copper chromite | 68.6 | 3.0 | 29.0 | 19.0 | 0.233 |

TABLE 3

| Temperature (°C.) | H$_2$ pressure (psig) | Conversion (%) | Selectivity (%) monopropylamine | dipropylamine | tripropylamine | Amines Productivity kg/kg catalyst/h |
|---|---|---|---|---|---|---|
| 200 | 2000 | 96 | 20.5 | 46.2 | 7.7 | 0.476 |
| 250 | 4000 | 99 | 2.7 | 44.4 | 17.9 | 0.429 |

TABLE 4

| Example | Catalyst | H$_2$ Pressure (psig) | Temp (°C.) | Time (h) | Conversion (%) |
|---|---|---|---|---|---|
| 1 | 0.5 g Pd/Re/HSAG + 2 g 4A zeolite | 4000 | 200 | 6 | 96 |
| 5 | 0.5 g Pd/Re/activated carbon + 2 g 4A zeolite | 4000 | 200 | 6 | 1 |

I claim:

1. A process for the production of an amine which process comprises reacting an amide with hydrogen at elevated temperature in the presence as catalyst of a composition comprising as a first component (i) a noble metal of Group VIII of the Periodic Table of the Elements, and (ii) rhenium, said first component being supported on a high surface area graphitised carbon, and as a second component either an alumina or a zeolite.

2. A process according to claim 1 wherein the amide is of the formula:

(I)

wherein R$^1$ is either hydrogen or a substituted or unsubstituted benzyl, aryl, aliphatic or cycloaliphatic group, and R$^2$ and R$^3$ are independently either hydrogen or substituted or unsubstituted aliphatic groups.

3. A process according to claim 2 wherein in the formula (I) R$^1$ is either hydrogen or an alkyl group.

4. A process according to claim 2 wherein in the formula (I) $R^2$ and $R^3$ are either hydrogen or an alkyl group.

5. A process according to claim 1 wherein the amide is either acetamide, propionamide or a fatty amide.

6. A process according to claim 1 wherein in the first component of the catalyst the noble metal of Group VIII is palladium or ruthenium.

7. A process according to claim 1 wherein the first component is modified by incorporation of a metal or metals of Group IA, Group IIA or Group IVA of the Periodic Table of the Elements.

8. A process according to claim 1 wherein the first component of the catalyst is prepared by a method comprising the steps of:
(A) impregnating a high surface area graphitised carbon support with a solution of a soluble Group VIII noble metal compound thermally decomposable/reducible to Group VIII noble metal and subsequently removing the solvent therefrom, and
(B) impregnating the Group VIII metal impregnated support with a solution in a solvent in which the Group VIII metal is substantially insoluble of a soluble rhenium compound thermally decomposable/reducible to rhenium metal and/or an oxide and thereafter removing the solvent therefrom.

9. A process according to claim 8 wherein the first component of the catalyst is activated by contact at elevated temperature with either hydrogen or a hydrogen/inert gas mixture for a period of from 1 to 20 hours.

10. A process according to claim 1 wherein the first component of the catalyst is prepared by a method comprising the steps of:
(A') impregnating a high surface area graphitised carbon support with a solution of a soluble Group VIII noble metal compound thermally decomposable/reducible to the Group VIII noble metal and subsequently removing the solvent therefrom,
(B') heating the Group VIII noble metal on the support, and
(C') impregnating the Group VIII noble metal impregnated support with a solution of a soluble rhenium compound thermally decomposable/reducible to rhenium metal and/or oxide and thereafter removing the solvent therefrom.

11. A process according to claim 10 wherein the first component of the catalyst is activated by contact at elevated temperature with either hydrogen or a hydrogen/inert gas mixture for a period of from 1 to 20 hours.

12. A process according to claim 1 wherein the second component of the catalyst is a zeolite which is a low silica aluminosilicate zeolite.

13. A process according to claim 12 wherein the zeolite is either zeolite type A or zeolite type Y.

14. A process according to claim 12 wherein the zeolite is a zeolite type A which is zeolite type 4A.

15. A process according to claim 1 wherein the elevated temperature is in the range from 150° to 300° C.

* * * * *